US008975465B2

(12) United States Patent
Hong et al.

(10) Patent No.: US 8,975,465 B2
(45) Date of Patent: Mar. 10, 2015

(54) DIAPER HAVING A WETNESS DETECTOR, SYSTEM THEREOF AND WETNESS DETECTING METHOD

(75) Inventors: Ruey-Shyan Hong, Taoyuan County (TW); Hung-Wen Chang, New Taipei (TW); Chu-Hsuan Chen, Hsinchu (TW); Su-Jan Lee, Taipei (TW); Biing-Shiun Huang, Taipei (TW); Shwn-Jen Lee, Taipei (TW)

(73) Assignees: Industrial Technology Research Institute, Hsinchu (TW); National Yang-Ming University, Taipei (TW); Taipei Veterans General Hospital, Taipei (TW)

( * ) Notice: Subject to any disclaimer, the term of this patent is extended or adjusted under 35 U.S.C. 154(b) by 638 days.

(21) Appl. No.: 13/242,797

(22) Filed: Sep. 23, 2011

(65) Prior Publication Data

US 2013/0018231 A1 Jan. 17, 2013

(30) Foreign Application Priority Data

Jul. 15, 2011 (TW) .............................. 100125228 A

(51) Int. Cl.
*A61F 13/15* (2006.01)
(52) U.S. Cl.
USPC ............................ 604/361; 604/360; 604/359
(58) Field of Classification Search
USPC .............................. 604/361, 360, 359, 385.01
See application file for complete search history.

(56) References Cited

U.S. PATENT DOCUMENTS

| 4,356,818 A | 11/1982 | Macias et al. |
| 4,653,491 A | 3/1987 | Okada et al. |
| 5,264,830 A | 11/1993 | Kline et al. |
| 6,580,013 B1 | 6/2003 | Belloso |
| 6,774,800 B2 | 8/2004 | Friedman et al. |
| 6,916,968 B2 * | 7/2005 | Shapira et al. ................ 604/361 |
| 7,141,715 B2 | 11/2006 | Shapira |
| 7,176,344 B2 | 2/2007 | Gustafson et al. |
| 7,250,547 B1 | 7/2007 | Hofmeister et al. |
| 7,295,125 B2 | 11/2007 | Gabriel |
| 7,355,090 B2 | 4/2008 | Ales, III et al. |

(Continued)

FOREIGN PATENT DOCUMENTS

| CN | 1226855 A | 8/1999 |
| CN | 2364870 Y | 2/2000 |

(Continued)

OTHER PUBLICATIONS

Online Reference: Potty MD, "Wet Stop", http://www.wetstop.com (Jul. 20, 2011).

(Continued)

*Primary Examiner* — Jacqueline F. Stephens
(74) *Attorney, Agent, or Firm* — Muncy, Geissler, Olds & Lowe, P.C.

(57) ABSTRACT

A diaper having wetness detectors, a system thereof and a wetness detecting method are adapted to detect the excreting status of an animal. The diaper includes a first set of contacts and a second set of contacts which are constituted by conductive material. The first set of contacts and the second set of contacts are respectively disposed on proximal and distal area of the diaper corresponding to the excretory organ of the animal. A detecting circuit detects the electrical property of the first set of contacts and the second set of contacts and then determines the excretion status of the animal to be a reference for a caregiver.

11 Claims, 14 Drawing Sheets

(56) References Cited

U.S. PATENT DOCUMENTS

| | | | |
|---|---|---|---|
| 7,394,391 | B2 | 7/2008 | Long |
| 7,477,156 | B2 | 1/2009 | Long et al. |
| 7,489,252 | B2 | 2/2009 | Long et al. |
| 7,498,478 | B2 | 3/2009 | Long et al. |
| 7,595,734 | B2 | 9/2009 | Long et al. |
| 7,649,125 | B2 | 1/2010 | Ales, III et al. |
| 7,654,396 | B2 | 2/2010 | Takeno et al. |
| 7,700,821 | B2 | 4/2010 | Ales, III et al. |
| 2004/0230172 | A1 | 11/2004 | Shapira |
| 2007/0046482 | A1 | 3/2007 | Chan et al. |
| 2007/0252713 | A1 | 11/2007 | Rondoni et al. |
| 2007/0270774 | A1 | 11/2007 | Bergman et al. |
| 2008/0058743 | A1 | 3/2008 | Cohen et al. |
| 2009/0157023 | A1 | 6/2009 | Song et al. |

FOREIGN PATENT DOCUMENTS

| | | |
|---|---|---|
| CN | 2768733 Y | 4/2006 |
| CN | 101320009 A | 12/2008 |
| CN | 101449154 A | 6/2009 |
| CN | 201414881 Y | 3/2010 |
| CN | 201438982 U | 4/2010 |
| EP | 0 850 631 A1 | 7/1998 |
| JP | 2002-224093 A | 8/2002 |
| JP | 2006-263046 A | 10/2006 |
| TW | 422088 | 2/2001 |
| TW | 485808 | 5/2002 |
| TW | 200511976 | 4/2005 |
| TW | M353004 | 3/2009 |
| TW | M356498 | 5/2009 |
| TW | M361327 | 7/2009 |
| TW | M364508 | 9/2009 |
| TW | I327063 | 7/2010 |
| TW | M387657 | 9/2010 |
| TW | M390779 | 10/2010 |

OTHER PUBLICATIONS

Online Reference: Anzacare, "DRI Sleeper", http://www.dri-sleeper.com/ (Jul. 20, 2011).
Online Reference: Ideas for Living, Inc., "Potty Pager", http://www.pottypager.com (Mar. 10, 2010).
Online Reference: StarChild/Labs, "The Sleep Dry Alarm", http://www.sleepdryalarm.com (Jul. 20, 2011).
Online Reference: Malem Medical, "Enuresis Alarm", http://www.malem.co.uk Jul. 20, 2011.
Siden, et al., "The "Smart" Diaper Moisture Detection System", Microwave Symposium Digest, (Jun. 2004), pp. 659-662, vol. 2.
Wai, et al., "Towards Developing Effective Continence Management Through Wetness Alert Diaper: Experiences, Lessons Learned, Challenges and Future Directions", Pervasive Computing Technologies for Healthcare, (Mar. 2010), pp. 1-8.
Online Reference: Malem Medical, "Ultimate Bed-Side Alarm", http://www.malem.co.uk, (Jul. 20, 2011).
Online Reference: Malem Medical, "Wireless Alarm + Record Wetness Sensor and Toilet Trainer", http://malem.co.uk, (Jul. 20, 2011).
Ang, et al., "Wireless Intelligent Incontinence Management System Using Smart Diapers", ECTI-CON, 5$^{th}$ International Conference, (2008), pp. 69-72.
Online Reference: Nytone Medical Products, (Get Control Again, Nytone), http://www.nytone.com/get-control-again-2/ (Jul. 20, 2011).
Online Reference: UK Electronics, (ENURAD 400), http://www.enurad.com/, (Sep. 22, 2011).
Online Reference: Koregon Enterprises, Inc., Stop Bed Wetting with Nite Train-r), http://www.nitetrain-r.com/products, (Jul. 20, 2011).

* cited by examiner

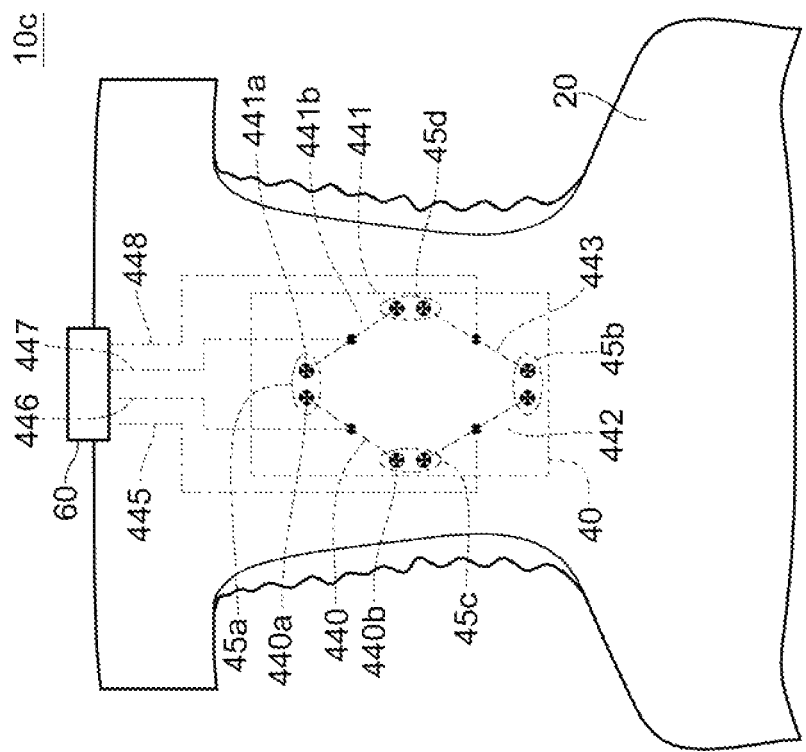

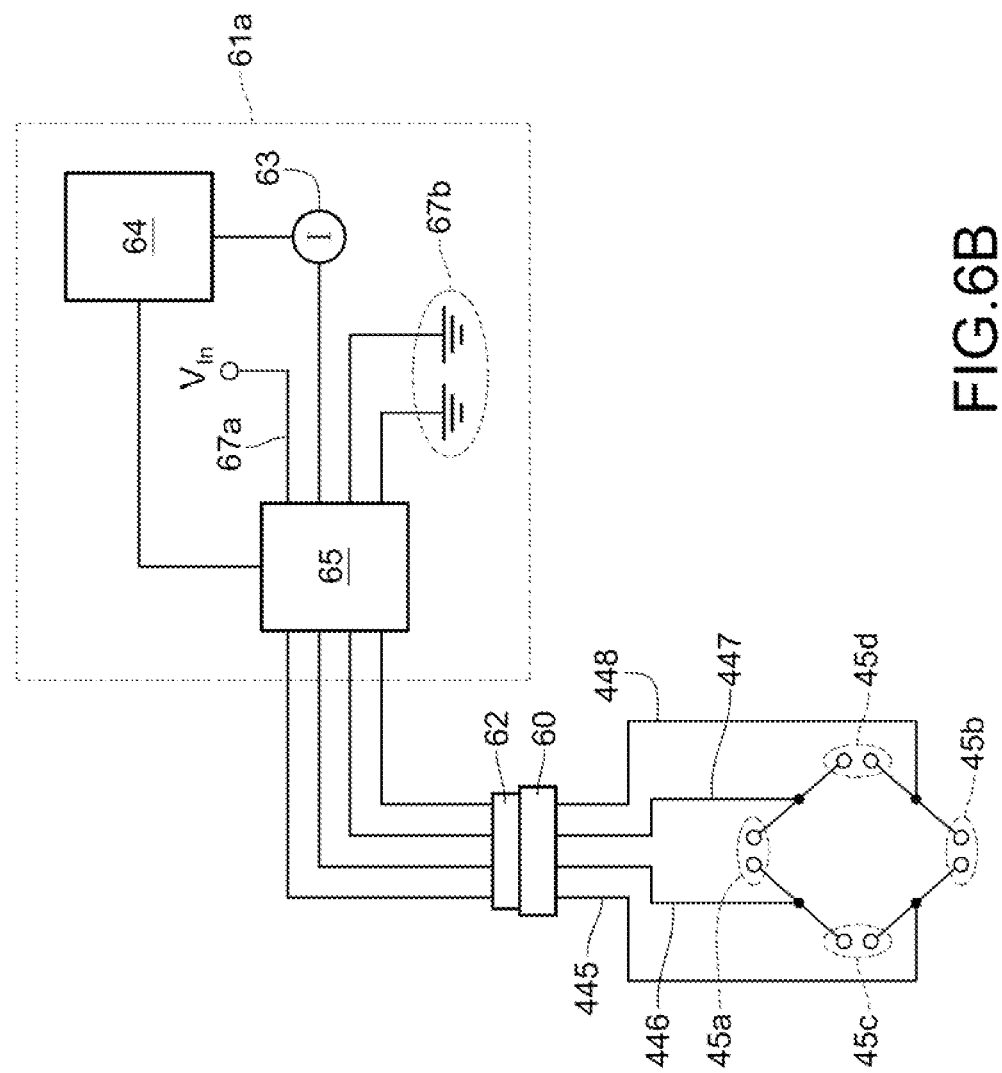

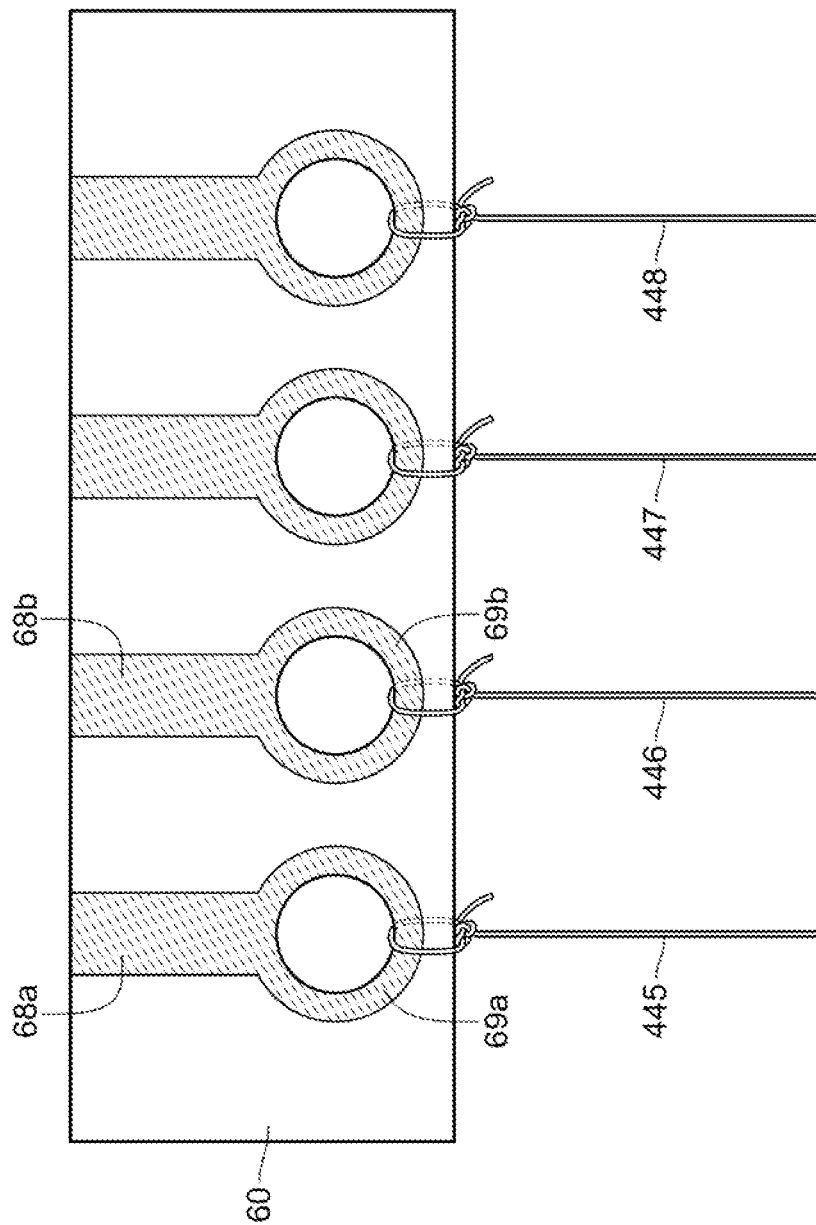

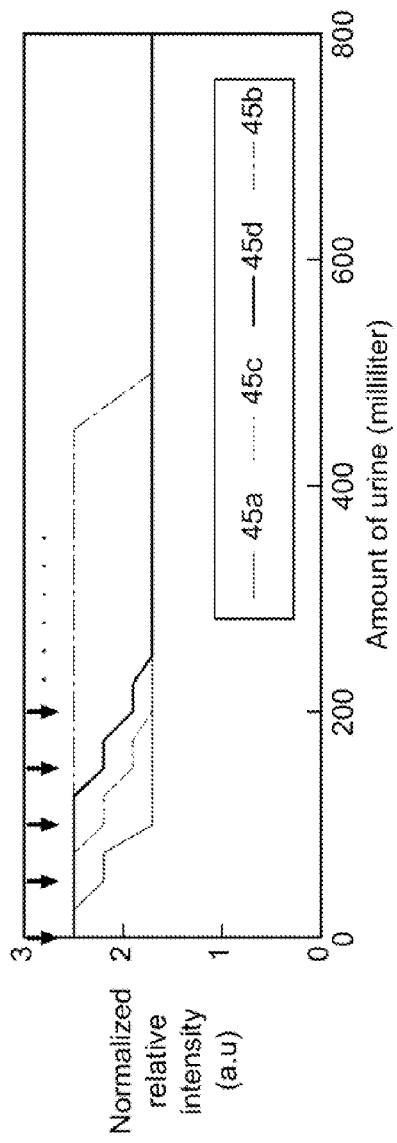
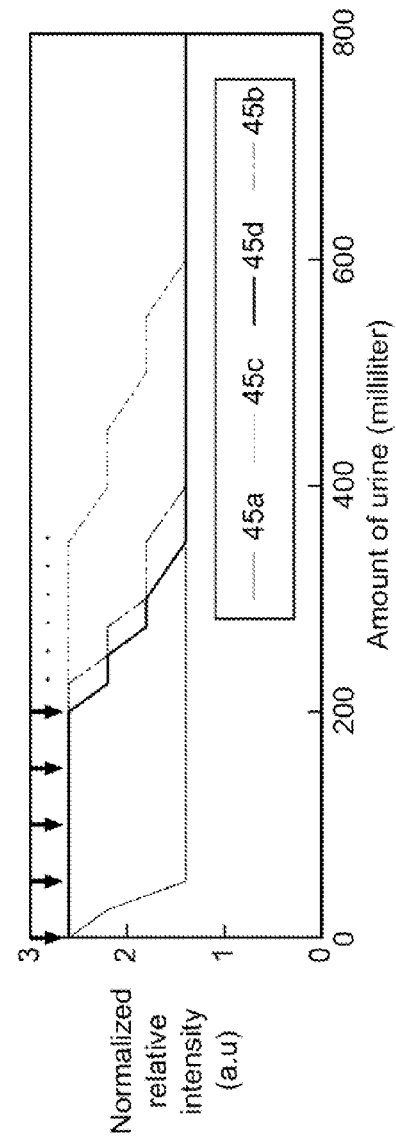

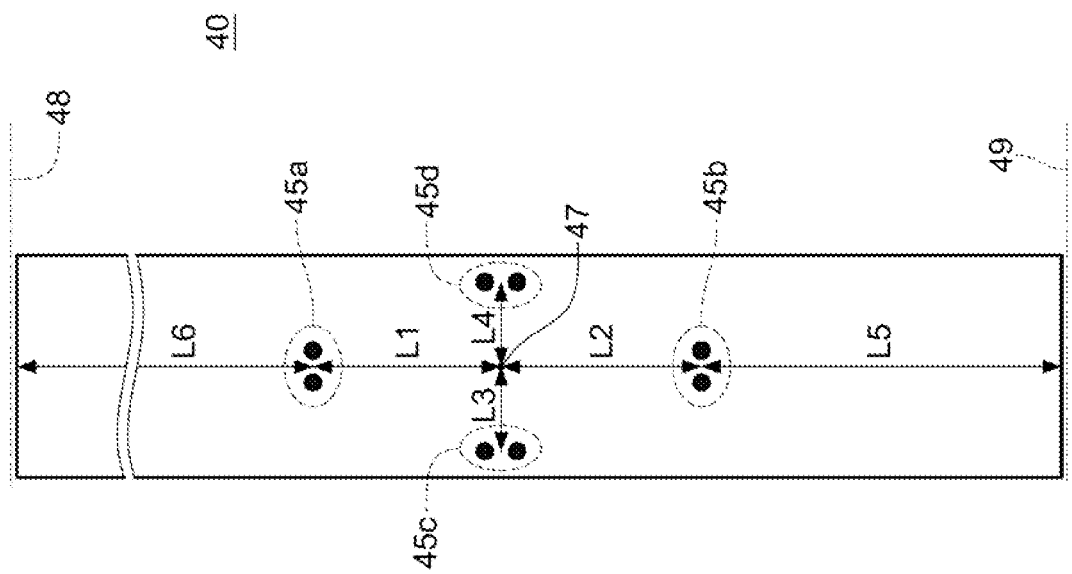

DIAPER HAVING A WETNESS DETECTOR, SYSTEM THEREOF AND WETNESS DETECTING METHOD

CROSS-REFERENCE TO RELATED APPLICATIONS

This non-provisional application claims priority under 35 U.S.C. §119(a) on Patent Application No(s). 100125228 filed in Taiwan, R.O.C. on Jul. 15, 2011, the entire contents of which are hereby incorporated by reference.

BACKGROUND

1. Technical Field

The disclosure relates to a diaper having wetness detectors, a system thereof and a wetness detecting method.

2. Related Art

The technology of disposing a detection device in a diaper to acquire information about whether the diaper should be changed has already been developed for years. Such detection devices may be electrode-lead type (applicable from the characteristic of electrical conductivity), coil type or chemical type. The electrode lead type was disclosed in ROC Utility Model Patent No. 422088, entitled "Paper diaper with a urination or excretion annunciator device". In this patent, two conductive flat metal foils may be sandwiched between a waterproof layer and an absorption body of the paper diaper to serve as sensors. The outside parts of the two metal foils extend away from the front curvy side-edge of the paper diaper to connect to a controller. The controller is triggered as the two metal foils are conducted by the water absorbed by the absorption body when the paper diaper gets wet due to urination or excretion. Therefore, the efficacies such as easy fabrication, automatic mass production and cost down are achieved, and the problems of health safety and environmental protection are avoided.

The electrode lead type was also disclosed in U.S. Pat. No. 7,700,821, entitled "Method and device for determining the need to replace an absorbent article". The coil type was disclosed in U.S. Pat. No. 7,141,715, entitled "System and method for assessing fluid distribution in a urine detection network". The chemical type was disclosed in US Publication, Patent Application No. 20090157023, entitled "Urine volume hydration test".

SUMMARY

The disclosure is a diaper having wetness detectors, a system thereof and a diaper wetness detecting method adapted to detect an excretion status of an animal.

According to an embodiment, a diaper having wetness detectors comprises an inner layer, an absorption layer, a detection layer and an outer layer. The inner layer is disposed at an excretory organ of an animal. The detection layer and the absorption layer are sandwiched between the inner layer and the outer layer. The detection layer comprises conductive wires. The conductive wires form a first set of contacts and a second set of contacts. A distance between the first set of contacts and the excretory organ is smaller than another distance between the second set of contacts and the excretory organ.

According to an embodiment, a diaper wetness detecting system comprises a diaper, detection circuit and management host. The diaper comprises an inner layer, an absorption layer, a detection layer and an outer layer. The inner layer is disposed at an excretory organ of an animal. The detection layer and the absorption layer are sandwiched between the inner layer and the outer layer. The detection layer comprises conductive wires. The conductive wires form a first set of contacts and a second set of contacts. A distance between the first set of contacts and the excretory organ is smaller than another distance between the second set of contacts and the excretory organ. The detection circuit is electrically connected to the conductive wires and outputs a contact signal when the electrical property of the first set of contacts or the second set of contacts exceeds a threshold value. The management host displays an excretion status according to the contact signal.

According to an embodiment, a diaper wetness semi-quantitative detecting method comprises: disposing a diaper at an excretory organ of an animal, in which the diaper comprises a first set of contacts and a second set of contacts, a distance between the first set of contacts and the excretory organ is smaller than another distance between the second set of contacts and the excretory organ; sensing electrical properties of the sets of contacts and outputting a contact signal; searching in a lookup table for an excretion status corresponding to the contact signal according to the contact signal; and outputting the excretion status.

BRIEF DESCRIPTION OF THE DRAWINGS

The disclosure will become more fully understood from the detailed description given herein below for illustration only, and thus are not limitation of the disclosure, and wherein:

FIG. 6A is a schematic structural plan view of a diaper according to a fourth embodiment of the disclosure;

FIG. 6B is a schematic circuit block diagram of a detection circuit of the diaper according to the fourth embodiment of the disclosure;

FIG. 6C is a schematic structural view of a first connector of the diaper according to the first embodiment of the disclosure;

FIG. 8A and FIG. 8B are schematic views of experimental results of the diaper according to the second embodiment of the disclosure;

FIG. 9 is a schematic enlarged plan view of a detection layer of a diaper according to the disclosure;

DETAILED DESCRIPTION

The detailed features and advantages of the disclosure are described below in great detail through the following embodiments, the content of the detailed description is sufficient for those skilled in the art to understand the technical content of the disclosure and to implement the disclosure there accordingly. Based upon the content of the specification, the claims, and the drawings, those skilled in the art can easily understand the relevant objectives and advantages of the disclosure.

Figure 1:
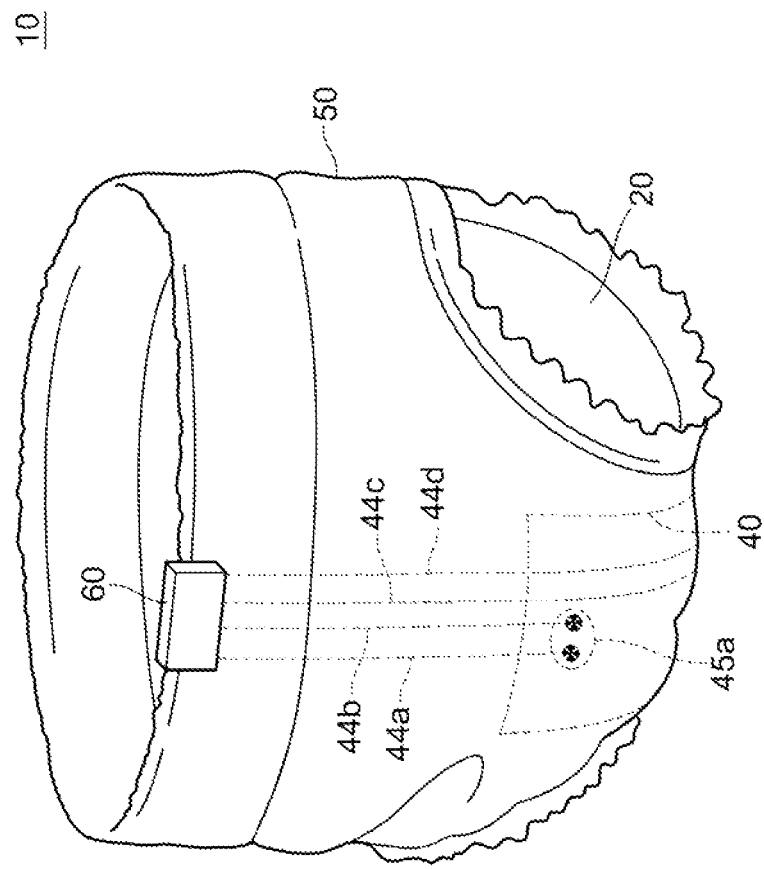
FIG. 1 is a schematic perspective view of a diaper according to a first embodiment of the present disclosure.
Figure 2:
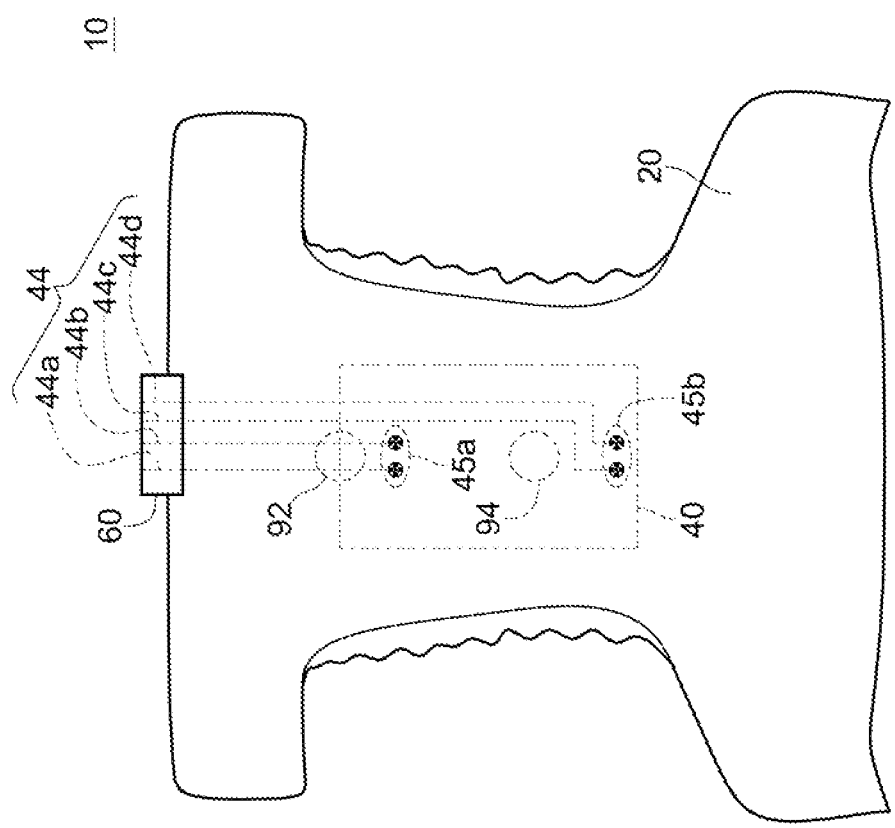
FIG. 2 is a schematic structural plan view of the diaper according to the first embodiment of the disclosure.

First, FIG. 1 and FIG. 2 are respectively a schematic perspective view and a schematic structural plan view of a diaper according to a first embodiment of the disclosure. The diaper having a wetness detector 10 is applicable to sensing an excretion status of an animal. The animal may be a human, a cat, a dog and a livestock, but is not limited to the above-mentioned animals. The sensing of the excretion status may be sensing urine or sensing excrement, but is not limited to the above-mentioned excretion. The excretion status refers to, but is not limited to, "whether excretion occurs" or "an excretion amount". Although a human is taken as an example for illustration in the following embodiments, the disclosure is not limited thereto.

Figure 3:
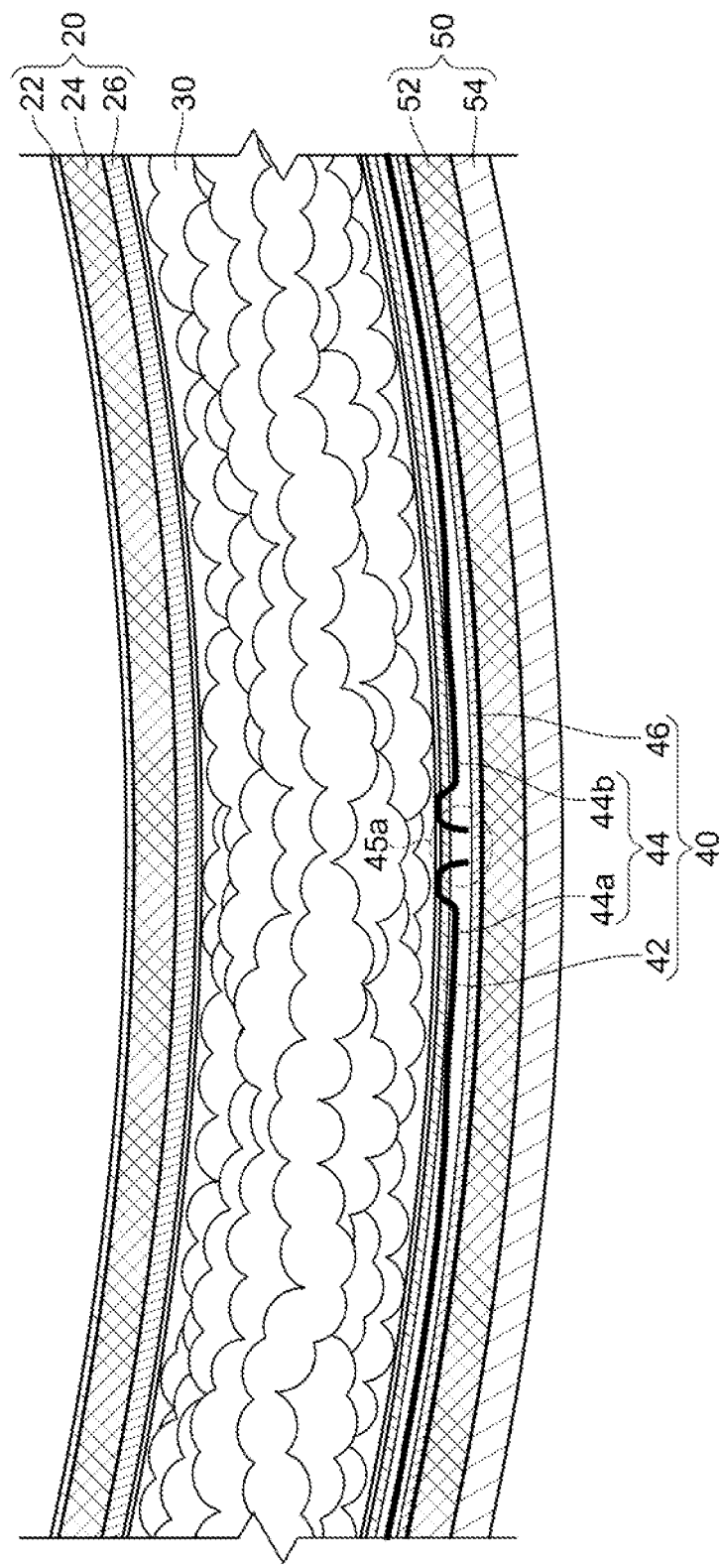
FIG. 3 is a schematic structural view of a partial section of the diaper according to the first embodiment of the disclosure.

FIG. 3 is a schematic structural view of a partial section of the diaper according to the first embodiment of the disclosure. A diaper 10 comprises an inner layer (also referred to as a diaper inner layer) 20, an absorption layer 30, a detection layer 40, and an outer layer (also referred to as a diaper outer layer) 50.

The inner layer 20 is disposed at an excretory organ of an animal. The excretory organ may be the urethra or the anus of an animal. The inner layer 20 being disposed at the excretory organ of the animal may be the inner layer 20 covering, surrounding, circling or wrapping the urethral orifice or anus. Taking a human body as an example, the inner layer 20 may be a layer of the diaper 10 which is in contact with the human body. Usually, the area of the inner layer 20 is greater than the size of an opening of the urethral orifice or anus, or even the inner layer 20 may at the same time wraps the urethral orifice, anus and a part of the buttocks; however, the disclosure is not limited thereto. Referring to FIG. 2, the indication 92 in FIG. 2 represents a position corresponding to a urethral orifice of the human body, and the indication 94 represents a position corresponding to an anus of the human body. In this embodiment, the illustration is given by taking the example of sensing an excretion status of urine excreted from a urethral orifice (excretory organ), and the urethral orifice (excretory organ) is represented by the indication 92 for ease of illustration.

The absorption layer 30 is also referred to as a water absorption layer, which is sandwiched between the inner layer 20 and the outer layer 50 for absorbing a body fluid (urine) discharged by an animal (human body).

The detection layer 40 is also sandwiched between the inner layer 20 and the outer layer 50. According to the embodiment in FIG. 3, the detection layer 40 is sandwiched between the absorption layer 30 and the outer layer 50. However, the disclosure is not limited thereto, and the detection layer 40 may be sandwiched between the inner layer 20 and the absorption layer 30.

The detection layer 40 comprises a number of conductive wires 44a and 44b, 44c and 44d (for the ease of illustration, the conductive wires are generally numbered as 44). The conductive wires 44a and 44b, 44c and 44d form a first set of contacts 45a and a second set of contacts 45b. A distance between the first set of contacts 45a and the urethral orifice (excretory organ) 92 is smaller than another distance between the second set of contacts 45b and the urethral orifice 92. In other words, the first set of contacts 45a is disposed at a proximal end and the second set of contacts 45b is disposed at a distal end. The proximal end here refers to a position closer to the urethral orifice 92. The distal end refers to a position further away from the urethral orifice 92 or is near another excretory organ (such as an anus), for example, the distal end is at the indication 94 or around the indication 94.

It could be known that when a user urinates, the electrical property of the first set of contacts 45a changes. The electrical property may be a resistance value or a voltage value, but is not limited in the above-mentioned electrical property. That is to say, before the user urinates, the first set of contacts 45a is in a dry state and no conductor exists. After the user urinates, the absorption layer 30 absorbs the urine and a part of urine permeates among the first set of contacts 45a and, then, the first set of contacts 45a is in a partially conductive state. Therefore, the resistance value before urination is greater than the resistance value after urination. Next, the amount of urinary output also affects the electrical property of the first set of contacts 45a. For example, after the amount of the urinary output increases, the amount of urine between the first set of contacts 45a also increases accordingly, so the resistance value between the first set of contacts 45a decreases as the amount of urine increases. When the amount of urine keeps increasing but the resistance value of the first set of contacts 45a no longer decreases (the resistance value at this time may be referred to as a saturation value), it may be estimated that the urine of the water absorption layer 30 close to the proximal end already reaches a saturated state. Therefore, the amount of the urine urinated by the user (excretion status) may be estimated by the electrical property of the first set of contacts 45a.

Moreover, the amount of the urinary output also affects the amount of the urine permeated among the second set of contacts 45b. That is, if the amount of the urine is smaller, no urine may exist among the second set of contacts 45b, so that the resistance value of the second set of contacts 45b is still at initial state. If the amount of urine is larger, the resistance value of the second set of contacts 45b decreases. When the resistance value of the second set of contacts 45b reaches the saturation value, the front portion and the rear portion of the diaper may be regarded as being soaked and, therefore, it is needed to replace the diaper.

As can be seen from the above illustration, the current diaper wetness (the amount of the discharged body fluid) of the user may be estimated according to the electrical properties of the first set of contacts 45a and the second set of contacts 45b, and in subsequent embodiments, a current posture of the user may also be known according to such electrical properties.

Next, refer to FIG. 3 again. The inner layer 20 comprises a permeable layer 22, a first textile structure layer 24 and a urine distribution layer 26. The outer layer 50 comprises a second textile structure layer 52 and a water isolation layer 54 in order from inside to outside. The material of the permeable layer 22 may be hydrophilic nonwoven fabric for permeation of body fluid, but is not limited to the above-mentioned material. The material of the first textile structure layer 24 and the second textile structure layer 52 may be porous nonwoven fabric, but is not limited to the above-mentioned material. The material of the urine distribution layer 26 may be hydrophilic nonwoven fabric for spreading (horizontal diffusion) the body fluid instead of gathering at a single position, but is not limited to the above-mentioned material. The material of the water isolation layer 54 may be waterproof nonwoven fabric or plastic (polyvinyl chloride, PVC), but is not limited to the above-mentioned material.

The detection layer 40 comprises a first insulation layer 42 and a second insulation layer 46. The conductive wires 44a and 44b, 44c and 44d are sandwiched between the first insulation layer 42 and the second insulation layer 46, and the conductive wires 44a and 44b located at the first set of contacts 45a and the second set of contacts 45b leave and pierce the first insulation layer 42 to return to a position between the first insulation layers 42 and second insulation layers 46 (that is, the weave is the simple plan knit). In other words, the conductive wires 44a and 44b located at the first set of contacts 45a and the second set of contacts 45b are exposed at the first insulation layer 42. In this embodiment, a portion of each conductive wires 44a and 44b leaves the first insulation layer 42, and a portion of each conductive wires 44a and 44b pierces the first insulation layer 42. However, the disclosure is not limited thereto, and the conductive wires 44a and 44b may also leave and enter the second insulation layer 46 (that is, exposed at the second insulation layer 46).

Next, the conductive wires 44a and 44b, 44c and 44d may be blending stainless steel conductive wires (such as conductive metal threads, conductive metal foils, conductive metal strips, gold, silver, copper, tin or alloys thereof). In addition to that the conductive wires 44a and 44b, 44c and 44d may have conductivity at two ends, the conductive wires 44a and 44b, 44c and 44d may not be wrapped with insulation material. In this embodiment, the above-mentioned first set of contacts 45a or the second set of contacts 45b may be not formed of any endpoints of the conductive wires 44a and 44b, 44c and 44d. In addition, the contacts may be located at the position where is the smallest distance between two adjacent conductive wires 44a and 44b, 44c and 44d.

The size of the detection layer 40 may be the same as that of the inner layer 20 or the outer layer 50. In some embodiments, the size of the detection layer 40 may be smaller than that of the inner layer 20 and the outer layer 50. For example, as shown in FIG. 1 or FIG. 2, the detection layer 40 is only near the excretory organ, and covers the positions near the urethral orifice and the anus.

Figure 4:
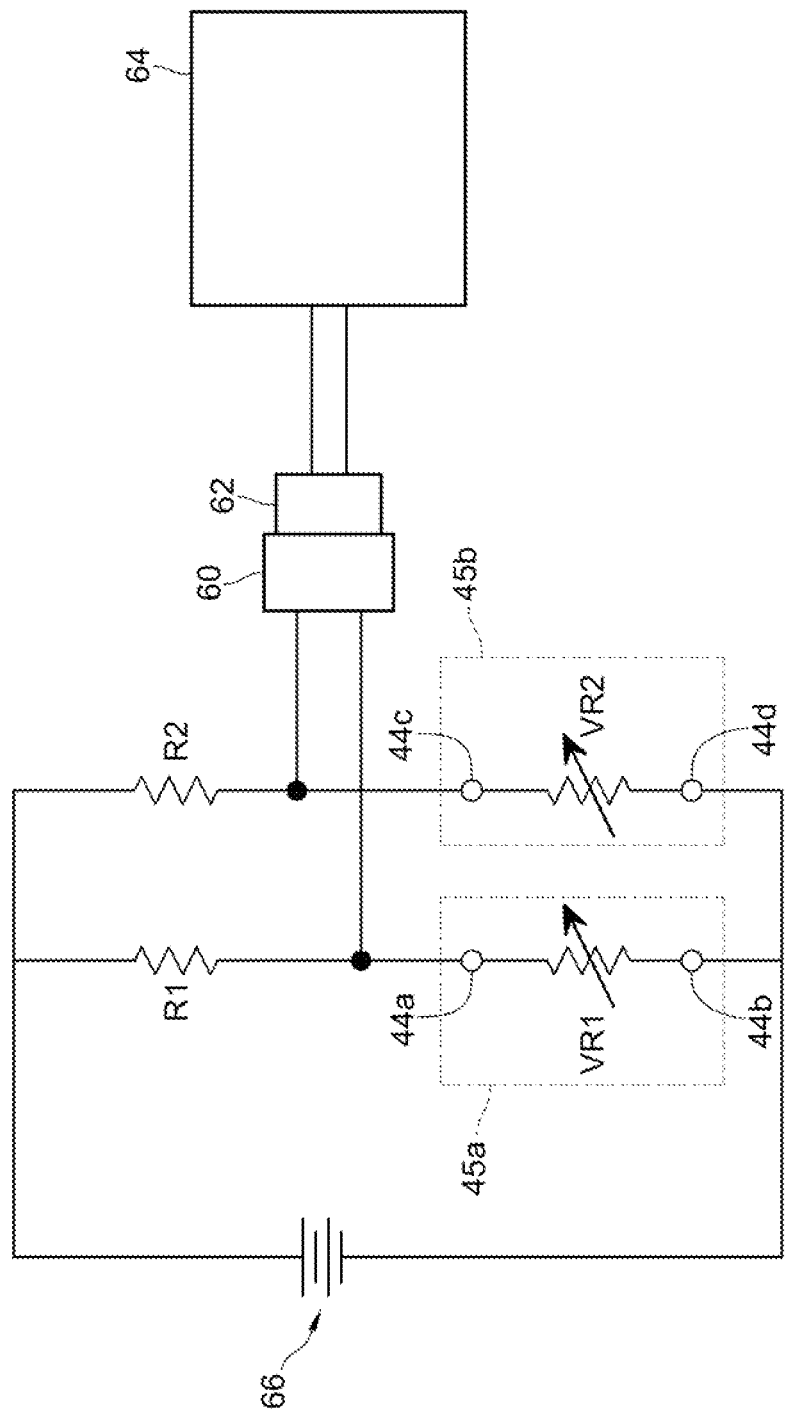
FIG. 4 is a schematic circuit block diagram of a detection circuit of the diaper according to the first embodiment of the disclosure.

FIG. 4 is a schematic circuit block diagram of a detection circuit of the diaper according to the first embodiment of the present disclosure. As shown in FIG. 4, the diaper 10 may further comprise a detection circuit 61. The detection circuit 61 is electrically connected to the conductive wires 44a and 44b, 44c and 44d and the detection circuit 61 outputs a contact signal when the electrical property of the first set of contacts 45a or the second set of contacts 45b exceeds a threshold value. The threshold value may be the saturation value but is not limited to the above-mentioned value. The output contact signal may be any electric signal, sound, vibration or light. By taking the light as an example, the detection circuit 61 drives a light element to emit a ray as the contact signal when the electrical property exceeds the threshold value. The light element may be a light emitting diode, but is not limited to the above-mentioned element. The detection circuit 61 may be disposed at the diaper 10. In some embodiments, and the detection circuit 61 may be a separation part from the diaper 10.

The detection circuit comprises a power source 66, a first resistor R1, a second resistor R2, a first connector 60, a second connector 62 and a control circuit 64. The first resistor R1 and first set of contacts 45a are connected in series and then are electrically connected to the power source 66. The second resistor R2 and the second set of contacts 45b are connected in series and then are electrically connected to the power source 66. The control circuit 64 is electrically connected to a serial connection point (that is, as shown by the number 44a) of the first resistor R1 and the first set of contacts 45a and another serial connection point (that is, as shown by the number 44c) of the second resistor R2 and the second set of contacts 45b by the first connector 60 and the second connector 62, and outputs a contact signal according to the electrical properties of the two serial connection points.

As can be seen from FIG. 4, the resistance values of the first set of contacts 45a and the second set of contacts 45b change according to the degree of wetness (with different amount of the body fluid). Therefore, it may be regarded as that variable resistor VR1 and variable resistor VR2 exist between the first set of contacts 45a and the second set of contacts 45b. As the resistance values of the variable resistors VR1 and VR2 change, the divided voltages of the two serial connection points change accordingly. The control circuit 64 may then obtain the wetness degree of the diaper 10 based on the divided voltages of the two serial connection points.

Figure 5B:
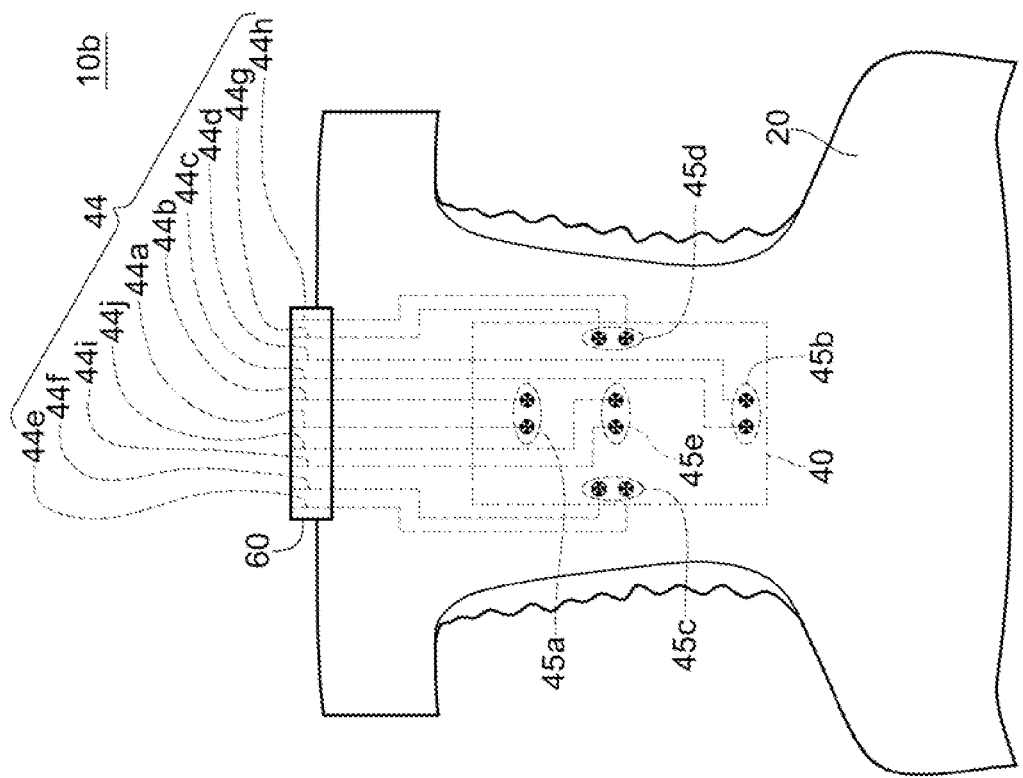
FIG. 5B is a schematic structural plan view of a diaper according to a third embodiment of the disclosure.
Figure 5A:
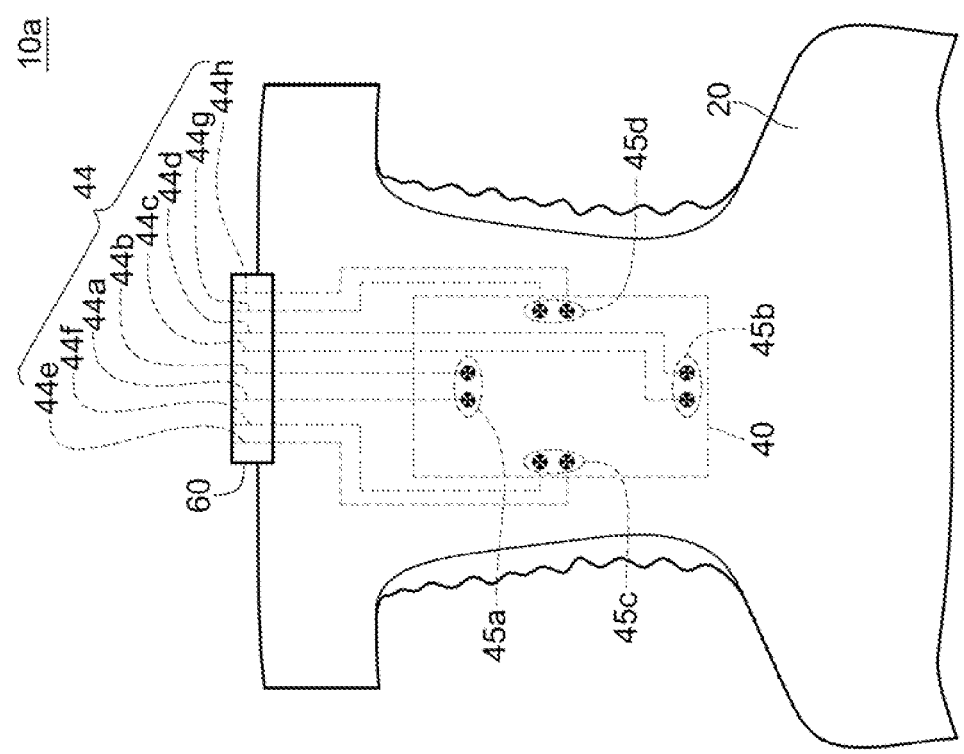
FIG. 5A is a schematic structural plan view of a diaper according to a second embodiment of the present disclosure.

Moreover, FIG. 5A is a schematic structural plan view of a diaper according to a second embodiment of the disclosure. Compared with the diaper 10 in the first embodiment, the diaper 10a further comprises a third set of contacts 45c and a fourth set of contacts 45d. The third set of contacts 45c and the fourth set of contacts 45d are formed of conductive wires 44e, 44f, 44g and 44h. The third set of contacts 45c and the fourth set of contacts 45d are located at two sides of a connecting line extending from the first set of contacts 45a to the second set of contacts 45b (that is, the left side and the right side in FIG. 5A). The distances between the third set of contacts 45c and the fourth set of contacts 45d across the connecting line between the first set of contacts 45a and the second set of contacts 45b may change based on the design demands and requirements.

As shown in FIG. 5A, when body fluid enters the first set of contacts 45a, and a user is in a state of lying on back, the urine flows towards the second set of contacts 45b due to the gravity thereof. At this time, the resistance values of the third set of contacts 45c and the fourth set of contacts 45d might not change or may decrease slightly. Then the signal of 45b decreases last. When the user lies on left side (that is, presses the bed with the left shoulder), the urine enters the first set of contacts 45a. The time point that the resistance of the third set of contacts 45c starts to drop is earlier than the another time point that the resistance values of the second set of contacts 45b. The voltage of the fourth set of contacts 45d drops last. Therefore, according to the time points of changes in the electrical properties or the degrees of the electrical property values (for example, the resistance value or the voltage value) change at the different sets of contacts, the degree of wetness in the diaper and the current posture of the user may be obtained.

In addition, if the electrical property of the first set of contacts 45a does not reach the saturation value but the electrical property of the second set of contacts 45b already changes or the change in electrical property of the second set of contacts 45b is greater than that of the first set of contacts 45a, it may be that the user has excreted watery stool (diarrhea).

As can be seen from the above content, there are many cases of urination or defecation by the user, the electrical property corresponding to each state is slightly different. The detection circuit 61 may obtain different electrical property values or the time points when the electrical property values change of all sets of contacts 45a, 45b, 45c and 45d by tests and experiments to estimate the current excretion status of the diaper (a diaper wetness degree, that is so-called semi-quantitative analysis) instead of only acquiring the single result whether the diaper needs to be changed.

FIG. 5B is a schematic structural plan view of the diaper according to a third embodiment of the disclosure. It can be seen from FIG. 5B that the conductive wires 44i and 44j further form a fifth set of contacts 45e. As the fifth set of contacts 45e is disposed, the detection circuit 61 may obtain more information about the wetness degree of the diaper to provide more accurate estimation result.

Next, FIG. 6A is a schematic structural plan view of a diaper according to a fourth embodiment of the disclosure. It may be seen from FIG. 6A that the manner of disposing the conductive wires 44 in the diaper 10c is different from those in the first, second and third embodiments. In this embodiment, the conductive wires 44 comprise a number of contact wires 440, 441, 442 and 443 and a number of guide wires 445, 446, 447 and 448. Each of the contact wires 440, 441, 442 and 443 has two endpoints. By taking the contact wire 440 as an example, the two endpoints are respectively 440a and 440b. The contact wire 441 has two endpoints 441a and 441b. The adjacent two of the endpoints 440a, 440b, 441a and 441b form one of the sets of contacts 45a, 45b, 45c and 45d. For example, the adjacent endpoints 440a and 441a form the first set of contacts 45a, and so on. A distance between the adjacent endpoints 440a and 441a may be, but is not limited to, 0.1 cm to 1 cm. The guide wires 445, 446, 447 and 448 are respectively electrically connected to the contact wires 440, 441, 442 and 443 one to one. The guide wires 445, 446, 447 and 448 are then connected to the first connector 60 to be electrically connected to the detection circuit 61.

FIG. 6B is a schematic circuit block diagram of a detection circuit of the diaper according to the fourth embodiment of the present disclosure. As can be seen form FIG. 6B, the detection circuit 61a is electrically connected to guide wires 445, 446, 447 and 448 by the second connector 62. The detection circuit 61a comprises a control circuit 64, a switch element 65, a voltage input end 67a, a ground end 67b and a current measurement circuit 63. The voltage input end 67a provides a voltage source. The current measurement circuit 63 is used to measure a current value. The current measurement circuit 63 may be a current meter or a similar circuit. The switch element 65 may be a four-way switch. The guide wires 445, 446, 447 and 448 are electrically connected to the switch element 65 to be selectively electrically connected to the voltage input end 67a, the current measurement circuit 63 and the ground end 67b.

When the electrical property of the first set of contacts 45a needs to be measured, the control circuit 64 controls the switch element 65 to make the guide wire 446 electrically connected to the voltage input end 67a, make the guide wire 447 electrically connected to the current measurement circuit 63, and make the guide wires 445 and 448 are electrically connected to the ground end 67b. In such a manner, the voltage output by the voltage input end 67a flows to the current measurement circuit 63 through the first set of contacts 45a. At this time, after the conversion of the current measured by the current measurement circuit 63 and the voltage inputted by the voltage input end 67a (the voltage is divided by the current), the resistance (electrical property) of the first set of endpoints 45a is obtained. In other words, the control circuit 64 is used to control the switch element 65 to electrically connect one of the guide wires, which is the guide wire 446, to the voltage input end 67a; electrically connect another one of the guide wires, which is the guide wire 447, to the current measurement circuit 63, and electrically connect the other guide wires 445 and 448 to the ground end 67b.

Next, when the electrical property of the fourth set of contacts 45d needs to be measured, the control circuit 64 controls the switch element 65 to electrically connect the guide wire 447 to the voltage input end 67a; electrically connect the guide wire 448 to the current measurement circuit 63, and electrically connect the guide wires 445 and 446 to the ground end, and so on.

As can be seen from the fourth embodiment, each adjacent two of the contact wires 440, 441, 442 and 443 may form a set of contacts 45a, 45b, 45c or 45d. Through the combination with the guide wires 445, 446, 447 and 448, the detection circuit 61 only needs to measure the electrical property between the guide wires 446 and 447 to obtain the electrical property of the first set of contacts 45a, measure the electrical property between the guide wires 445 and 448 to acquire the electrical property of the second set of contacts 45b, and so on. Therefore, the first connector 60 may only use four contacts to obtain the electrical properties of four sets of contacts 45a, 45b, 45c and 45d. Compared with the second embodiment, the number of contacts of the first connector 60 in the fourth embodiment may be reduced by half (from 8 to 4). Similarly, if an analog-to-digital conversion element or a controller is disposed on the detection circuit 61, the number of elements or controller contacts may also be reduced by at least half. By taking the circuit in FIG. 6B as an example, the number of contacts of the controller may be reduced by half, and only one current measurement circuit 63 is needed.

FIG. 6C is a schematic structural view of a connector of the diaper according to the first embodiment of the present disclosure. As can be seen from FIG. 6C, the first connector 60 comprises conductive rings 69a and 69b and conductive contacts 68a, 68b. The guide wires 445, 446, 447 and 448 are respectively wound on the conductive rings 69a and 69b. The winding manner is not limited to knotting, hooking or rolling manner, as long as the objective of electrical connection is achieved. In addition, welding material may also be added at the windings to ensure the stability of the electrical connection thereof.

Furthermore, the conductive contacts 68a and 68b may be, but are not limited to, metal conductive foils (or referred to as gold fingers). The conductive rings 69a and 69b are electrically connected to the conductive contacts 68a and 68b in one-to-one manner, so the guide wires 445, 446, 447 and 448 are electrically connected to the conductive contacts 68a and 68b. When the first connector 60 is connected to the second connector 62, the guide wires 445, 446, 447 and 448 are guided to the detection circuit 61a.

Figure 7:
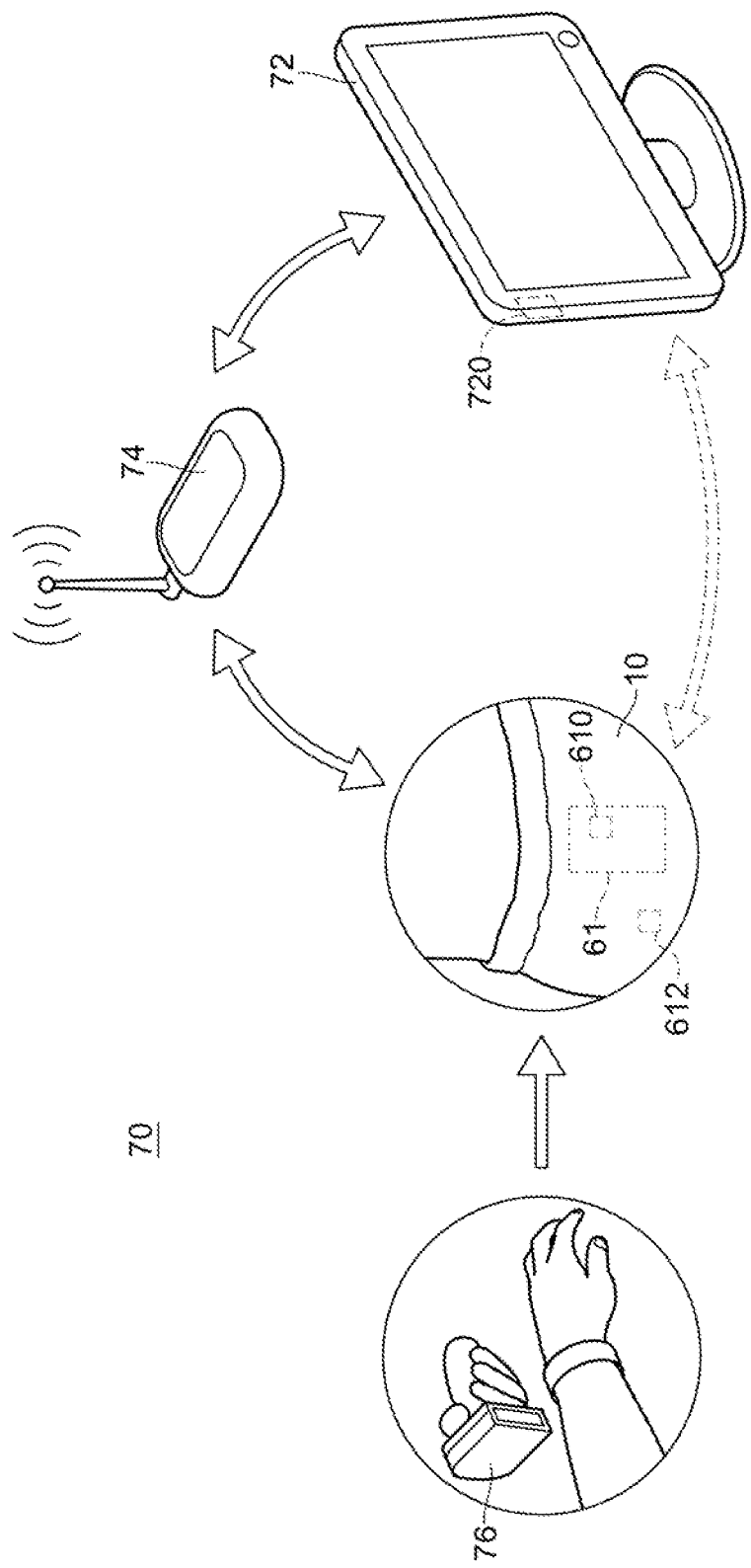
FIG. 7 is a schematic view of a diaper wetness management system according to the disclosure.

Moreover, FIG. 7 is a schematic view of a diaper wetness management system according to the disclosure. The diaper wetness management system 70 is applicable to sensing an excretion status of an animal and comprises a diaper 10, a detection circuit 61 and a management host 72. The detection circuit 61 may output a contact signal according to the electrical property of a first set of contacts 45a and/or a second set of contacts 45b (as shown in FIG. 2). The management host 72 displays an excretion status according to the contact signal. The management host 72 may be a notebook computer, a desktop computer, a handheld electronic device (for example, a mobile phone or a Personal Digital Assistant (PDA)) or a server, but is not limited to the above-mentioned management hosts. The diaper 10 may also be the diaper 10a, 10b or 10c in the second embodiment, third embodiment or fourth embodiment. By taking the second embodiment as an example, the management host 72 may collect the electrical properties of the first, second, third and fourth sets of contacts 45a, 45b, 45c and 45d from the diaper 10, and obtain a current diaper wetness status (or excretion status) of the diaper 10 by analysis or table lookup instead of only providing the information of whether the diaper needs to be changed.

As can be seen from the above illustration, the contact signal transmitted to the management host 72 may be the electrical property of a single set of contact or may also be the electrical properties of all sets of contacts. Of course, the contact signal may also comprise a time message to determine or estimate a current diaper wetness status based on the events in sequence and time differences of the events (for example, taking the changes of the electrical properties as such events).

The coupling between the management host 72 and the detection circuit 61 may be direct electrical connection or wireless connection (as shown by dotted lines in FIG. 7). If the detection circuit 61 and the management host 72 are connected in a wireless manner, the detection circuit 61 may comprise a first wireless transceiver 610 and the management host 72 may comprise a second wireless transceiver 720. The above-mentioned contact signal may be transmitted to the management host 72 through the first wireless transceiver 610 and the second wireless transceiver 720. In addition, the first wireless transceiver 610 and the second wireless transceiver 720 may also be coupled with a router 74.

Next, the diaper wetness management system 70 may further comprise a scanner 76 (for example, but not limited to a barcode reader). A medical worker (or an employee) may scan a recognition data (for example, a patient number or a patient ID number) of a human (for example, a patient) wearing the diaper 10 by using the scanner 76. Then the diaper wetness management system 70 combines the recognition data and the serial number of the diaper 10 into a recognition signal and transmits the recognition signal to the management host 72. The management host 72 may obtain the related information (for example, the electrical property of each set of contacts) of the current diaper 10 by querying the detection device 61 periodically. In addition, the detection device 61 may also actively transmit the recognition signal to the management host 72 when a certain event happens (such as when the electrical property of each set of contacts changes), then the management host 72 analyzes and displays the recognition signal.

The management host 72 may comprise a health history database. The health history database consists of basic information, such as health history, weight, height and age. Upon receiving the recognition signal, the management host 72 may search for the basic data, health history and anamnesis of the patient in the database according to the received recognition signal. The health history and the anamnesis include, for example, the age, body weight, examination results, medication administration record, dietary water amount and defecation and urination record of the patient, but are not limited to the above-mentioned records. The operation of the management host 72 and the health history database is illustrated below.

In addition, the diaper 10 may further comprise an input element 612. When being actuated, the input element 612 outputs an actuation signal. Then the management host 72 receives the actuation signal to output an alarm signal. The input element 612 may be, but is not limited to, a button. The button may be pressed by a caregiver, a nurse or a patient during defecation of the patient. When being pressed (actuated), the input element 612 outputs the actuation signal. Upon receiving the actuation signal, the management host 72 outputs an alarm signal immediately. The alarm signal may be an alarm displayed on a screen that the diaper needs to be changed, or a sound of changing the diaper emitted by a buzzer.

Next, FIG. 8A and FIG. 8B are schematic views of experimental results of the diaper according to the second embodiment of the disclosure. In this experiment, the diaper 10b in the second embodiment is adopted. In the experiment in FIG. 8A, a state that a patient lying on back (with the face up) urinates is simulated. In FIG. 8B, the experiment that the patient lies on the right side (that is, the right shoulder is in contact with the bed) and discharges urine (represented by the arrows from top to bottom in FIG. 8A) about 50 milliliter (cc) every three minutes is made. The horizontal axis in FIG. 8A and FIG. 8B represent the practical total urine discharge amount (that is, the amount absorbed by the diaper 10) and the vertical axis in FIG. 8A and FIG. 8B represent the normalized relative electrical property (for example, the voltage).

FIG. 8A shows the situations of changes of the electrical properties of all sets of contacts 45a, 45b, 45c and 45d after adding 50 milliliter (ml) of urine every three minutes. The thin solid line represents the electrical property value of the first set of contacts 45a. The center line represents the electrical property value of the second set of contacts 45b. The dotted line represents the electrical property value of the third set of contacts 45c. The thick solid line represents the electrical property value of the fourth set of contacts 45d. When the 50 milliliter urine is added for the first time (that is, the leftmost first downward arrow), as the first set of contacts 45a is the closest to the urethral orifice, the electrical property (resistance or voltage) of the first set of contacts 45a changes first, and the electrical properties of the other sets of contacts 45b, 45c and 45d are still the same. As time passes by, before the urine is added for the second time (that is, the leftmost second downward arrow), the electrical property of the first set of contacts 45a presents a stable state. Next, after the urine is added for the second time (that is, the leftmost second downward arrow), the electrical property of the first set of contacts 45a starts dropping again, and the electrical property of the third set of contacts 45c also starts to drop. As shown in FIG. 8A, when the electrical properties of the first, third and fourth sets of contacts 45a, 45c, 45d all drop to a saturation value, that is, all of the electrical properties no longer drops. After that the urine continues to be added for several times, the electrical property of the second set of contacts 45b starts to drop again. This phenomenon occurs because the second set of contacts 45b is the farthest set of contacts from the urethral orifice.

In addition, by observing in the above manner in FIG. 8B, it may be known that as the patient lies on the right side, the electrical property of the third set of contacts 45c is the last one to starts dropping. It may be also known from the above experiment that the semi-quantitative analysis and posture analysis may be achieved by the combination of the diaper 10 and the detection circuit 61.

Figure 8C:
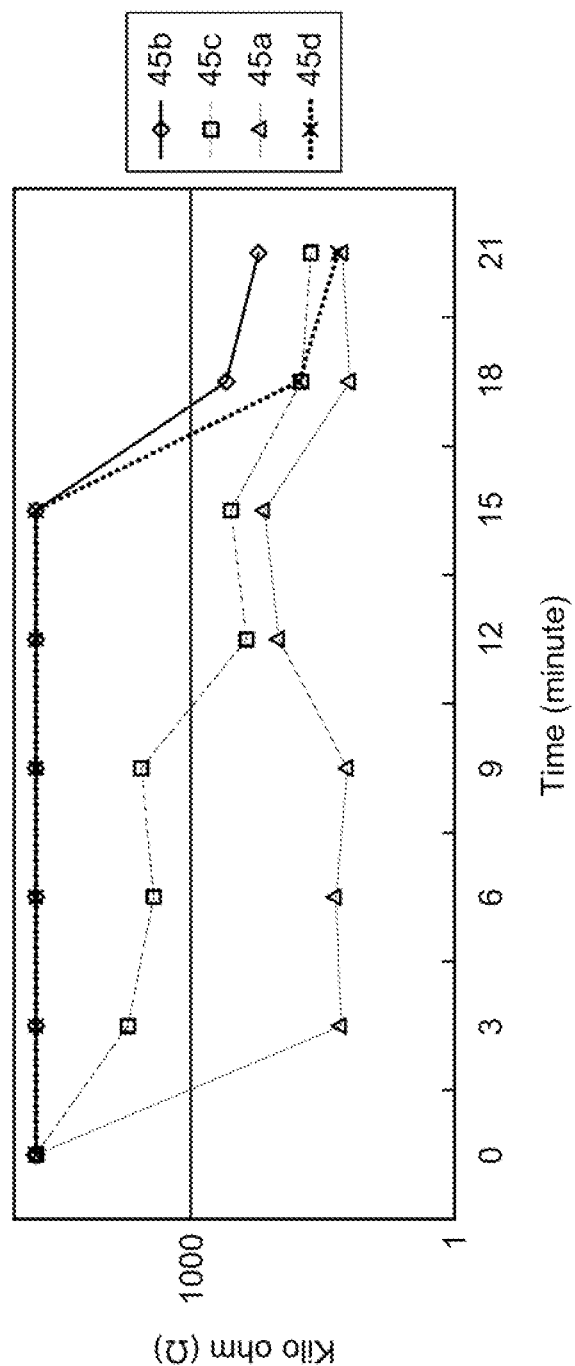
FIG. 8C is a schematic view of an experimental result of the diaper according to the fourth embodiment of the disclosure.

FIG. 8C is a schematic view of an experimental result of the diaper according to the fourth embodiment (FIG. 6A) of the disclosure. In this embodiment, 30 milliliter (ml) liquid is added at the position of the simulated urethral orifice every three minutes, and the electrical properties of all sets of contacts 45a, 45b, 45c and 45d are measured every three minutes. In the drawing of the experimental result, the horizontal axis is time with the unit of minute. The vertical axis is an impedance value with the unit of kiloohm (kΩ). As shown in FIG. 8C, the impedance of the first set of contacts 45a drops first and the slope of this interval is the steepest line in FIG. 8C. The start time point that the impedance of the third set of contacts 45c drops is close to that of the impedance of the first set of contacts 45a. However, the extent of the dropping impedance of the third set of contacts 45c is smaller than that of the first set of contacts 45a, and a stable internal exists between the two impedances. After 12 minutes, the impedance values of the first set of contacts 45a and the third set of contacts 45c are closer than other set of contacts. After 15 minutes, the impedances of the second set of contacts 45b and the fourth set of contacts 45d also drop and both impedances are relatively close to the impedance value of the first set of contacts 45a. Therefore, it may be acquired that the whole diaper is soaked and the critical time point of changing the diaper is reached.

For the implementation of the semi-quantitative analysis and posture analysis, experiments shall be made first before the diaper 10 is shipped from the factory. The experiments are made by using the posture and the amount of urine as variables to acquire a comparison table of electrical properties of all sets of contacts, the amount of urine and the posture, and then the comparison table is made into a lookup table. Therefore, both the detection circuit 61 and the management host 72 may estimate a current diaper wetness status (excretion status) and a posture through the lookup table after collecting the electrical property information of all sets of contacts 45a, 45b, 45c and 45d to provide more information to the caregiver.

The semi-quantitative analysis and posture analysis are illustrated by taking FIG. 8C as an example. In the above illustration of FIG. 8C, the different postures of the simulated dummy lies in bed wearing the diaper are not illustrated. However, according to the time sequence of changes of the electrical properties of all sets of contacts 45a, 45b, 45c and 45d, the lying posture may be estimated. It may be seen from FIG. 8C that the electrical property of the third set of contacts 45c changes earlier than the electrical property of the second set of contacts 45b, so that it may be assumed that the third set of contacts 45c is closer to the bed surface than the second set of contacts 45b. Indeed, in this experiment, the simulated dummy lies on a side with the left shoulder pressing the bed. Therefore, if the analysis of other postures needs to be acquired, several experiments of different postures may be made to acquire the data of several groups of changing time points and changing degrees of electrical properties of different postures to further make a posture lookup table.

Next, a volume of liquid absorbed in the diaper may be estimated according to the electrical properties of all sets of contacts 45a, 45b, 45c and 45d from FIG. 8C. For example, if there is no change in the electrical properties of the second set of contacts 45b and the fourth set of contacts 45d, the electrical property (impedance) of the first set of contacts 45a drops to about 500 ohms, and the impedance of the third set of contacts 45c drops to about 800 ohms (approximately the state between the twelfth minute and fifteenth minute in FIG. 8C), it may be estimated that the user might already discharge urine of about 120 milliliters to 150 milliliters (the premise is that the user is lying down on the left shoulder). Therefore, during the implementation, after experimental data of various different postures, liquid amounts and electrical property changes is established, the above-mentioned semi-quantitative lookup table may be established.

FIG. 9 is a schematic enlarged plan view of a detection layer of a diaper according to the disclosure. The detection layer 40 is taking the diaper in the fourth embodiment as an example, but is also applicable to the second or third embodiment. The positions where all sets of contacts 45a, 45b, 45c and 45d are disposed can be seen from FIG. 9. An intersection 47 refers to an intersecting position of the connecting line between the first and second sets of contacts 45a and 45b and another connection line between the third and fourth sets of contacts 45c and 45d. The distance from the intersection 47 to the first, second, third, fourth sets of contacts 45a, 45b, 45c and 45d (to a midpoint of the endpoints of two wires in the same set of contacts) are respectively L1, L2, L3 and L4. The distance between the first set of contacts 45a and the front edge 48 of the diaper is L6. The distance between the second set of contacts 45b and the rear edge 49 of the diaper is L5. The length of L4 plus L3 is smaller than or equal to the width of the diaper (L1 is 0.5 to 1.5 times of L2. Next, the intersection 47 may be either of the two positions of the urethral orifice corresponding to the indication 92 and the anus corresponding to the indication 94 in FIG. 2 or any position in the middle of the two positions).

Figure 10:
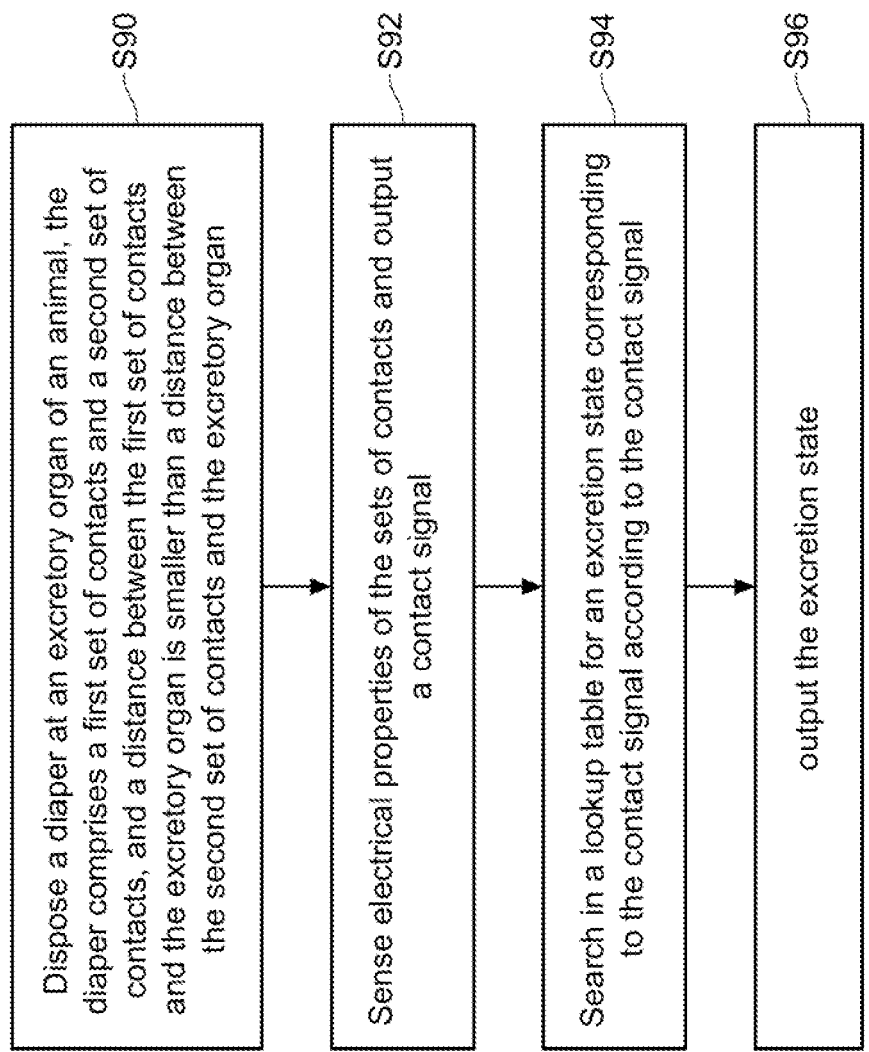
FIG. 10 is a schematic flow chart of a diaper wetness detecting method according to the disclosure.

FIG. 10 is a schematic flow chart of a diaper wetness detecting method according to the present disclosure. The diaper wetness detecting method is applicable to detecting excretion status of an animal. The method comprises the following steps.

Step S90: A diaper is disposed at an excretory organ of an animal. The diaper comprises a first set of contacts and a second set of contacts. A distance between the first set of contacts and the excretory organ is smaller than a distance between the second set of contacts and the excretory organ.

Step S92: Electrical properties of the first and second sets of contacts are sensed and a contact signal is output.

Step S94: According to the contact signal, an excretion status corresponding to the contact signal is searched in a lookup table.

Step S96: An excretion status is output.

In Step S90, the diaper may be the diaper 10, 10a, 10b or 10c in the first, second, third or fourth embodiment. In Step S92, the electrical property of each set of contacts in the diaper 10 is output in a signal manner. The signal may be the electrical property signal of a single set of contacts, or may also be electrical property signals of a number of sets of contacts or all sets of contacts. Of course, the time point that the electrical property of each set of contacts starts to change can also be output. Step S92 may be performed by the detection circuit 61.

In Step S94, upon receiving the contact signal, the management host 72 searches according to the contact signal in the lookup table for an excretion status corresponding to the contact signal. The excretion status may be a diaper wetness estimated through the lookup table or a wetness degree of each position of the diaper 10, but is not limited to the above-mentioned excretion status. Next, the excretion status is output in Step S96. For example, a display displays an amount of urine or a wetness degree at each position of the diaper.

In addition, if the wetness degree of the diaper is higher than a threshold value (for example, a saturation value), in Step (S96) of displaying the excretion status, a light emitting diode may also be driven to emit a light, or a buzzer is driven to emit an alarm sound.

In conclusion, the diaper 10 may acquire the electrical property value of each set of contacts by the two set of contacts respectively disposed at a far end and a near end. After the analysis of the electrical property values, sequences, time points, and duration that the electrical property values changes, the diaper wetness may be analyzed in a semi-quantitative manner. In addition, due to the design of disposing the conductive wires, the electrical properties of the sets of contacts may be detected more effectively and the wiring of the conductive wires and the contact number of the connectors may be simplified.

Figure 11:
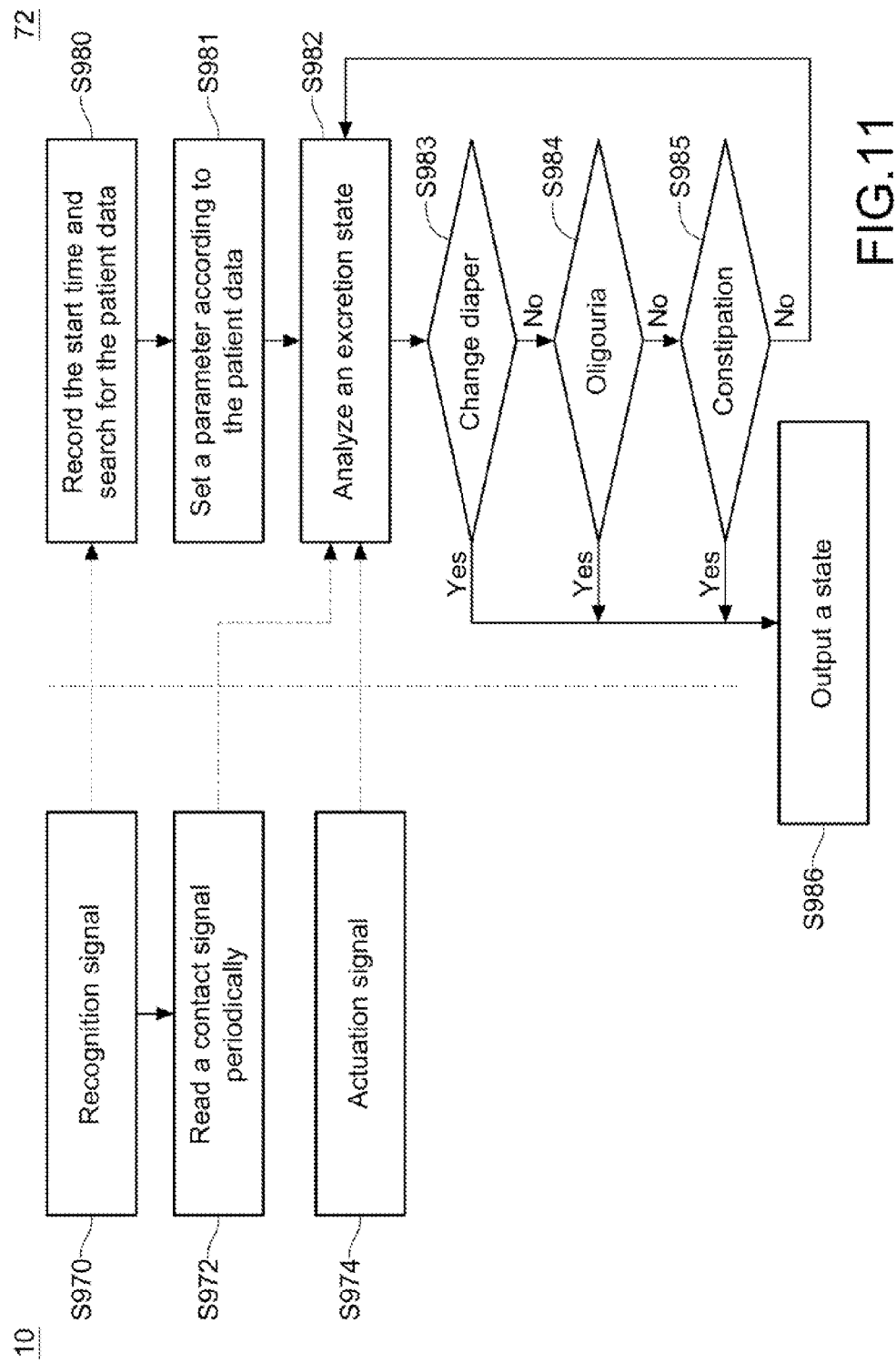
FIG. 11 is a schematic flow chart of an operation of a diaper wetness detecting system according to the disclosure.

For the interaction between the diaper 10 and the management host 72 in the diaper wetness management system 70, please refer to FIG. 7 in combination with FIG. 11. After a medical worker helps a patient to wear a diaper 10, the number of the diaper 10 and the recognition data of the patient may be scanned by using the scanner 76, and the number and recognition data are integrated into a recognition signal and transmitted the recognition signal to the management host 72 (Step S970). Upon receiving the recognition signal, the management host 72 may analyze the recognition signal, record the start time and search for the patient data in the database (Step S980). In such a manner, the management host 72 may synchronize the patient data, the diaper data and the data in the management host. Next, the management host 72 sets a parameter according to the patient data (for example, the body weight, age, dietary water amount, medical record and illness) (that is, Step S981). The parameter may be a normal range of an amount of urine, a normal urination frequency range, an anuresis time critical value and a constipation time critical value, but is not limited to the above-mentioned parameters. The parameter is used for providing information for the procedure of analyzing the excretion status in Step S982.

After scanning the diaper, a caregiver may initiate the operation of the diaper 10 (that is, the process turns to Step S972). This operation may be accomplished by a caregiver pressing a switch key disposed on the diaper, or the diaper 10 may be actuated by a signal emitted by the management host 72 after the management host 72 finishes Step S981. In Step S972, the diaper 10 may periodically retrieve the contact signal and transmit the contact signal to the management host 72. The management host 72 analyzes the excretion status by using the parameter and the contact signal (S982). Next, when the caregiver finds that the defecation event occurs to the patient, the caregiver may actuate the input element 612, and the diaper 10 transmits the actuation signal (Step S974) to the management host 72. The actuation signal is used for providing information for analyzing the excretion status (or referred to as a diaper state) in Step S982.

After Step S982, the management host 72 performs determination in Steps S983, S984 and S985. In Step S983, it is determined whether the diaper needs to be changed. When the analysis result shows that the urinary output already exceeds the normal range of amount of urine, the state needs to be displayed as "Change diaper" (Step S986). If the urinary output does not exceed the normal range of amount of urine, it is determined that whether the analysis result is higher than a critical value of anuresis time. If the analysis result is higher than the critical value of anuresis time, the state is displayed as anuresis (or non-urinary alert) (Step S986). If the analysis result is not higher than the critical value of anuresis time, it is further determined whether the analysis result exceeds the critical value of constipation time. If the analysis result exceeds the critical value of constipation time, the state is displayed as constipation (Step S986). If the analysis result does not exceed the critical value of constipation time, the process returns to Step S982 to continue to analyze the excretion status (diaper state).

In Step S986, the state (the excretion status or the diaper state) may be output at the management host 72 (by displaying or triggering an alarm bell). Alternatively, the management host 72 outputs the excretion status to the diaper or another management center and the diaper or management center then displays the excretion status. In addition, when the determine results in Steps S983, S984 and S985 are all null, the excretion status may also be output. The output content might be information such as the amount of urine absorbed by the current diaper, the frequency that the patient urinates and the posture of the patient.

What is claimed is:

1. A diaper having wetness detectors, comprising:
    an inner layer, disposed at an excretory organ of an animal;
    an outer layer;
    an absorption layer, sandwiched between the inner layer and the outer layer; and
    a detection layer, sandwiched between the inner layer and the outer layer and comprising a plurality of conductive wire sets forming a plurality of contacts, each of the conductive wire sets having a first conductive wire and a second conductive wire, the first conductive wire and the second conductive wire of the same conductive wire set being electrically connected;
    wherein the first conductive wire has a first endpoint, the second conductive wire has a second endpoint, each two adjacent first endpoint and second endpoint of the different conductive wire sets form one of the contacts, the contacts disposed around a first area of the detection layer corresponded to a second area of the inner layer for contacting the excretory organ.

2. The diaper according to claim 1, wherein the detection layer comprises:
    a first insulation layer; and
    a second insulation layer, wherein the conductive wire sets are sandwiched between the first insulation layer and the second insulation layer, and at contacts the conductive wires are exposed at the first insulation layer.

3. The diaper according to claim 1, wherein the inner layer comprises a permeable layer, a first textile structure layer and a urine distribution layer in sequence from inside to outside, and the outer layer comprises a second textile structure layer and a water isolation layer in sequence from inside to outside.

4. The diaper according to claim 1, wherein the detection layer has four the conductive wire sets forming four contacts, all of the four contacts disposed at the boundary of the first area of the detection layer corresponded to the second area of the inner layer for contacting the excretory organ.

5. The diaper according to claim 4, wherein the detection layer further has a fifth contact, and the fifth contact is located within the first area.

6. The diaper according to claim 4, wherein each conductive wire set has a guide wire.

7. The diaper according to claim 6, comprising a detection circuit, wherein the detection circuit comprises:
    a voltage input end, providing a voltage source;
    a ground end;
    a current measurement circuit, for measuring a current value;
    a switch element, electrically connected to the guide wires, the voltage input end, the ground end and the current measurement circuit; and
    a control circuit, for controlling the switch element to electrically connect one of the guide wires to the voltage input end, electrically connect another of the guide wires to the current measurement circuit, and electrically connect the other guide wires to the ground end.

8. The diaper according to claim 6, comprising a first connector, wherein the first connector comprises a number of conductive rings and a number of conductive contacts, the conductive rings are respectively electrically connected to the conductive contacts, and the guide wires are respectively wound at the conductive rings and respectively form electrical connection.

9. The diaper according to claim 1, further comprising a detection circuit, electrically connected to the conductive wires and outputting a contact signal when the electrical property of the contacts exceeds a threshold value.

10. The diaper according to claim 9, wherein the detection circuit comprises:
    a power source;
    a first resistor, connected to the one of contacts in series and then electrically connected to the power source;
    a second resistor, connected to the another one of contacts in series and then electrically connected to the power source; and a control circuit, electrically connected to the first resistor and the second resistor, for outputting the contact signal according to received electrical properties of the contacts connected by the first resister and the second resister.

11. The diaper according to claim 10, wherein the detection circuit comprises a light emitting element, and the control circuit actuates the light emitting element to provide the contact signal according to the electrical properties of the contacts connected by the first resister and the second resister.

* * * * *